(12) United States Patent
Bock et al.

(10) Patent No.: US 10,955,340 B2
(45) Date of Patent: Mar. 23, 2021

(54) METHOD FOR DETERMINING GLOSSINESS OF A PORTION OF A SKIN OF A USER

(71) Applicant: Henkel AG & Co. KGaA, Duesseldorf (DE)

(72) Inventors: Andreas Bock, Neuss (DE); Thomas Welss, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/695,765

(22) Filed: Nov. 26, 2019

(65) Prior Publication Data
US 2020/0187847 A1    Jun. 18, 2020

(30) Foreign Application Priority Data

Dec. 18, 2018    (DE) .................... 10 2018 222 122.7

(51) Int. Cl.
*G01N 21/57*    (2006.01)
*A61B 5/00*    (2006.01)
(Continued)

(52) U.S. Cl.
CPC .......... *G01N 21/57* (2013.01); *A61B 5/0064* (2013.01); *A61B 5/0077* (2013.01); *A61B 5/441* (2013.01); *A61B 5/6898* (2013.01); *G01N 21/21* (2013.01); *A45D 2044/007* (2013.01); *G06T 2207/30088* (2013.01)

(58) Field of Classification Search
CPC ..... A61B 5/0077; A61B 5/441; A61B 5/0059; A61B 5/442; A61B 5/443; A61B 5/6898; A61B 5/0075; G01N 21/21; G01N 21/25; G01N 21/57; A45D 2044/007; G01B 11/30; G06T 2207/30088; G06T 2207/30201
See application file for complete search history.

(56) References Cited

U.S. PATENT DOCUMENTS 5,198,875 A    3/1993   Bazin et al.
5,552,890 A *  9/1996   Nanna ................... G01N 21/57
                                                    101/211
(Continued)

FOREIGN PATENT DOCUMENTS

DE    59109413 T2        2/1996
JP    10281991 A  * 10/1998  ............. G01N 21/21
(Continued)

*Primary Examiner* — Gordon J Stock, Jr.
(74) *Attorney, Agent, or Firm* — Lorenz & Kopf, LLP (57) ABSTRACT

A method, system, and computer readable storage medium for determining a glossiness value of a skin of a user are provided. In an embodiment, a polarized light having a property value is emitted from a portable light source towards the portion of the skin of the user. The portable light source is coupled to a handheld device. The polarized light is cast on the portion of the skin of the user from the portable light source. Reflected light reflected from the portion of the skin of the user is measured using a sensor coupled to the handheld device. The reflected light has a property value. A ratio between the property values of the emitted polarized light and the measured reflected light is determined using a processor of the handheld device. The glossiness value of the portion of the skin of the user is determined based on the determined ratio.

20 Claims, 3 Drawing Sheets

(51) Int. Cl.
*G01N 21/21* (2006.01)
*A45D 44/00* (2006.01)

(56) References Cited

U.S. PATENT DOCUMENTS

| | | | | |
|---|---|---|---|---|
| 7,336,810 | B2 * | 2/2008 | Fujii | A61B 5/0059 |
| | | | | 356/369 |
| 7,872,754 | B2 * | 1/2011 | Wadman | G01N 21/49 |
| | | | | 356/445 |
| 8,695,610 | B2 * | 4/2014 | Samain | A45D 44/005 |
| | | | | 132/200 |
| 9,443,131 | B2 * | 9/2016 | Yamanashi | G06K 9/00 |
| 9,953,237 | B2 * | 4/2018 | Yamanashi | H04N 5/2256 |
| 10,281,267 | B2 * | 5/2019 | Masuda | G01N 21/21 |
| 10,638,968 | B2 * | 5/2020 | Yoshida | G06T 7/0012 |
| 10,743,769 | B2 * | 8/2020 | Yoshida | A61B 5/0077 |
| 2016/0098614 | A1 | 4/2016 | Yamanashi | |
| 2020/0113441 | A1 * | 4/2020 | Varghese | A61B 5/7278 |
| 2020/0113507 | A1 * | 4/2020 | Varghese | G01N 21/21 |
| 2020/0249161 | A1 * | 8/2020 | Mueller | G06Q 30/0631 |

FOREIGN PATENT DOCUMENTS

| | | | | |
|---|---|---|---|---|
| JP | 2014087464 | A * | 5/2014 | |
| WO | 2012020043 | A1 | 2/2012 | |
| WO | WO-2018001727 | A1 * | 1/2018 | ........... A61B 5/6898 |
| WO | 2018073266 | A1 | 4/2018 | |

* cited by examiner

METHOD FOR DETERMINING GLOSSINESS OF A PORTION OF A SKIN OF A USER

CROSS-REFERENCE TO RELATED APPLICATION

This application claims priority to German Patent Application No. 10 2018 222 122.7, filed Dec. 18, 2018, which is incorporated herein by reference in its entirety.

TECHNICAL FIELD

The present disclosure relates to the field of characterization of skin properties, and more particularly to a method for determining the glossiness of skin in order to determine the most relevant beauty care products suitable for a current skin condition.

BACKGROUND

It is commonplace in skin care to have a wide range of cosmetic products designed in particular for different types of skin. Skin can for example vary in color, presence of wrinkles, size of pores, presence of sweat or fatty substances such as sebum or other secretions, and presence of bacteria such as those leading to acne.

The appearance of skin may change from day to day and require a regular observation to determine which skin care products are most suitable to convey the appearance desired by a user.

Among the many parameters that influence the appearance of skin, before or after application of skin care products such as creams or coloration products, glossiness is particularly relevant. Glossiness of skin may vary from one day to the next and be further influenced by outside conditions such as temperature or air humidity.

Generally, people consult skin care professionals or attend points of sale in order to have their skin gloss measured. Dedicated portable gloss-meters have been specifically designed for such professionals. These gloss-meters comprise a light source and two sets of detectors to detect light reflected by skin and light scattered by skin. A particular illumination setup requires mirrors to keep the portable device small enough to be holdable with a hand. The costs of having a dedicated device prevent users from acquiring such a gloss-meter and using it at home on a regular basis. Users thus cannot easily monitor the evolution of the gloss of their skin and cannot easily select the most suitable cosmetic products based on the current glossiness of their skin.

Accordingly, it is desirable to provide a method to enable a simpler and more affordable determination of the glossiness value of the skin of a user. Furthermore, other desirable features and characteristics will become apparent from the subsequent detailed description and the appended claims, taken in conjunction with the accompanying drawings and the foregoing technical field and background.

BRIEF SUMMARY

Methods, systems and computer readable storage mediums for determining a glossiness value of a skin of a user are provided. In accordance with an embodiment, a method for determining a glossiness value of a portion of a skin of a user comprises emitting a polarized light having a property value from a portable light source towards the portion of the skin of the user. The portable light source is coupled to a handheld device. The polarized light is cast on the portion of the skin of the user from the portable light source. Reflected light reflected from the portion of the skin of the user is measured using a sensor coupled to the handheld device. The reflected light has a property value. A ratio between the property value of the emitted polarized light and the property value of the measured reflected light is determined using a processor of the handheld device. The glossiness value of the portion of the skin of the user is determined based on the determined ratio. The determined glossiness value is outputted.

In accordance with another embodiment, a system for determining a glossiness value of a portion of a skin of a user is provided. The system comprises a portable light source configured to emit polarized light having a property value towards the portion of the skin of the user so that the polarized light is cast on the portion of the skin of the user from the portable light source. A sensor is configured to measure reflected light reflected from the portion of the skin of the user, the reflected light having a property value. A handheld device comprises a processor configured to determine a ratio between the property value of the emitted polarized light and the property value of the measured reflected light and determine the glossiness value of the portion of the skin of the user based on the determined ratio. The portable light source and the sensor are physically coupled to the handheld device.

In accordance with a further embodiment, a non-transitory computer readable storage medium embodying a computer program product is provided. The program product comprises a program for determining a glossiness value of a portion of a skin of a user. The program is configured to emit a polarized light having a property value from a portable light source towards the portion of the skin of the user. The portable light source is coupled to a handheld device. The polarized light is cast on the portion of the skin of the user from the portable light source. The program also is configured to measure reflected light reflected from the portion of the skin of the user using a sensor coupled to the handheld device, the reflected light having a property value. The program is further configured to determine a ratio between the property value of the emitted polarized light and the property value of the measured reflected light using a processor of the handheld device. The processor also is configured to determine the glossiness value of the portion of the skin of the user based on the determined ratio, and output or trigger an output of the determined glossiness value.

BRIEF DESCRIPTION OF THE DRAWINGS

The various embodiments will hereinafter be described in conjunction with the following drawing figures, wherein like numerals denote like elements, and.

DETAILED DESCRIPTION

The following detailed description is merely exemplary in nature and is not intended to limit the disclosure or the application and uses of the subject-matter as described herein. Furthermore, there is no intention to be bound by any theory presented in the preceding background or the following detailed description.

To overcome the drawbacks of the prior art, the various embodiments provide a method for determining a glossiness value of a portion of a skin of a user, the method comprising:

emitting a polarized light of known properties from a portable light source towards a portion of the skin of the user, the portable light source being arranged on a handheld device, the polarized light being directly cast on the portion of the skin of the user from the portable light source;

measuring reflected light that has interacted with the portion of the skin of the user using a sensor arranged on the handheld device;

determining a ratio between properties of the emitted polarized light and properties of the measured reflected light using a processor of the handheld device;

determining the glossiness value of the portion of the skin of the user based on the determined ratio, and outputting or triggering an outputting of the determined glossiness value.

The method in accordance with various embodiments renders the determination of the glossiness of the skin of a user more accessible by using a handheld device to process optical information collected on the skin of the user. The light source and camera can be integral with the handheld device or be for example separate elements that can be arranged on the handheld device, for example by sticking them or clipping them on the surface of the handheld device.

Unlike dedicated devices from the prior art, the method as contemplated herein does not require mirrors to direct light towards the skin of the user but can cast light directly onto the skin of the user. The angle of incidence on the skin of the emitted light can also be adjusted by changing the orientation of the light source and/or camera.

The term "handheld device" advantageously refers to a portable phone, a tablet or a smart watch for example.

In an exemplary embodiment, the term "properties" when referring to the emitted polarized light or the reflected light comprises intensity of light, which is generally used when determining gloss values in prior art. In another embodiment, it comprises spectrum information about the light.

The term "glossiness value" can refer to a qualitative description of the glossiness of skin (low, medium, high) or correspond to a value according to a scale used to measure glossiness of skin. Gloss units may be used for example to express the glossiness value. Gloss units can typically correspond to the ratio of reflected to incident light of the portion of the skin of the user compared to the same ratio obtained for a gloss reference material, such as black glass of known refractive index. The terms "glossiness" and "gloss" are interchangeable as used herein.

The way glossiness is determined is described in prior art literature; typically, incident light arrives with an angle of about 60° on the skin of the user. Specular reflection is detected and the ratio of the intensity of incident light over reflected light is used as an indication of gloss. The conversion into units is done by comparing this ratio to a reference standard.

According to an embodiment, the portable light source is integral with the handheld device.

According to an embodiment, the portable light source is part of a display of the handheld device, the method further comprising:

activating a part of the display of the handheld device in order to emit the polarized light towards the portion of the skin of the user.

In an exemplary embodiment, the display of the handheld device, which can be a portable phone, a tablet or a smart watch for example, is used as the portable light source. A special program may trigger the activation of the whole display or just a portion thereof to cast light directly onto the skin of the user. The properties of the thus emitted light (intensity, spectrum) can also be adjusted, or cast according to a pre-programmed sequence on the skin of the user.

According to an embodiment, the method further comprises:

activating different parts of the display of the handheld device differing by a distance separating the different parts of the display of the handheld device from the sensor.

The spatial extent of the display of the handheld device, which can for example be a portable phone, a tablet or a smart watch for example, offers the opportunity of activating only one portion or a plurality of portions of the display at a time, to adjust the incident angle of the light that is cast on the skin of the user. The respective distance between a camera and the light source can thus be changed to test different illumination configurations and to acquire several comparable measurements of the properties of light that has interacted with the skin of the user.

In particular it is possible to program an illumination sequence that for example activates portions of the display according to a pattern or sequence so that different incident angles for the light cast on the skin of the user are generated. To do so, in an embodiment, the portion of the display that is activated is a spot or a narrow band of light. Such a sequence activation can also help reduce the influence of the distance between the handheld device and the skin of the user. Indeed, when a user orients the display of the handheld device and the camera towards his skin, in a configuration comparable to a "selfie" mode, he does not have a fine control on the distance between the handheld device and his skin. By testing different illumination configurations, the method can overcome this disadvantage and acquire measurements for a range of incident angles that remain substantially the same between different uses of the handheld device.

According to an embodiment, the different parts of the display of the handheld device are activated sequentially.

According to an embodiment, the polarized light of known properties is cast on a portion of the skin of the user with an incident angle comprised between about 10° and about 750°.

According to an embodiment, the method further comprises:

measuring light scattered by the portion of the skin of the user.

According to an embodiment, the scattered light is measured with a camera of the handheld device.

Measuring the scattered light provides a further opportunity to improve the determination of the glossiness of the skin of the user. The signal acquired from scattered light may for example compensate the influence of skin color. For that purpose, a subtraction between the reflected light and the scattered light might be implemented before determining the glossiness of the portion of the skin of the user.

According to an embodiment, the handheld device is chosen from among: a portable phone, a tablet or a smart watch.

According to an embodiment, the method further comprises:
recording a glossiness value determined for the portion of the skin of the user at a first time;
recording a glossiness value determined for the portion of the skin of the user at a second time differing from the first time;
outputting an evolution of the glossiness of the portion of the skin of the user based on the glossiness value determined at the first time and the second time.

According to an embodiment, the method further comprises:
determining at least one recommended non-therapeutic skin care product for the portion of the skin of the user based on the determined glossiness value;
outputting a reference identifying the determined at least one recommended non-therapeutic skin care product.

In accordance with an embodiment, to determine a recommended skin care product, such as cosmetics or creams that change the appearance of the skin of the user, the method accesses a database that stores a correspondence between glossiness values and non-therapeutic skin care products that are deemed to be suitable for a given glossiness value. The typical effect that users might want to achieve is to reduce the glossiness of their skin.

It is further possible to query the effect the user wants to achieve prior to recommending the non-therapeutic skin care products, should the user want to achieve a different effect than the reduction of gloss. Inputs provided by the user can be used to access corresponding product descriptions in a database.

In accordance with another exemplary embodiment, a system for determining glossiness of a portion of a skin of a user is provided. The system comprises:
a portable light source, configured to emit polarized light of known properties towards the portion of the skin of the user, so that the polarized light is directly cast on the portion of the skin of the user from the portable light source;
a sensor, configured to measure reflected light that has interacted with the portion of the skin of the user;
a handheld device comprising a processor configured to:
determine a ratio between properties of the emitted polarized light and properties of the measured reflected light; and
determine the glossiness value of the portion of the skin of the user based on the determined ratio;
wherein the portable light source and the sensor are arranged on the handheld device or form an integral part thereof, the sensor being capable of transmitting information to the handheld device.

Such a system is particularly suitable for implementing the method described above in such a way that a user may repeatedly assess the glossiness of his skin without the need to attend a point of sale or consult a skin care professional. The various embodiments contemplated herein render the measurement of the glossiness of the skin of users more easily accessible. Users can therefore use the system contemplated herein on a regular basis to accumulate data on the evolution of the glossiness of their skin, in order to gain insight into the state of their skin and adapt their skin care daily routine accordingly, for example by selecting more suitable cosmetics compatible with their skin gloss or by choosing particular skin cleaning products, creams or moisturizing lotions.

In accordance with a further exemplary embodiment, a non-transitory computer readable storage medium having stored thereon a computer program comprising instructions for execution of a method for determining a glossiness value of a portion of a skin of a user as described above is provided.

In other words, a computer program product comprising instructions for execution of a method for determining a glossiness value of a portion of a skin of a user as described above is provided.

The various embodiments contemplated herein provide a portable device to determine a glossiness value of a user's skin easily. This allows users to monitor the glossiness of their skin (at any part thereof) on a regular basis, eliminating the need to attend a point of sale or to acquire costly equipment.

Figure 1:
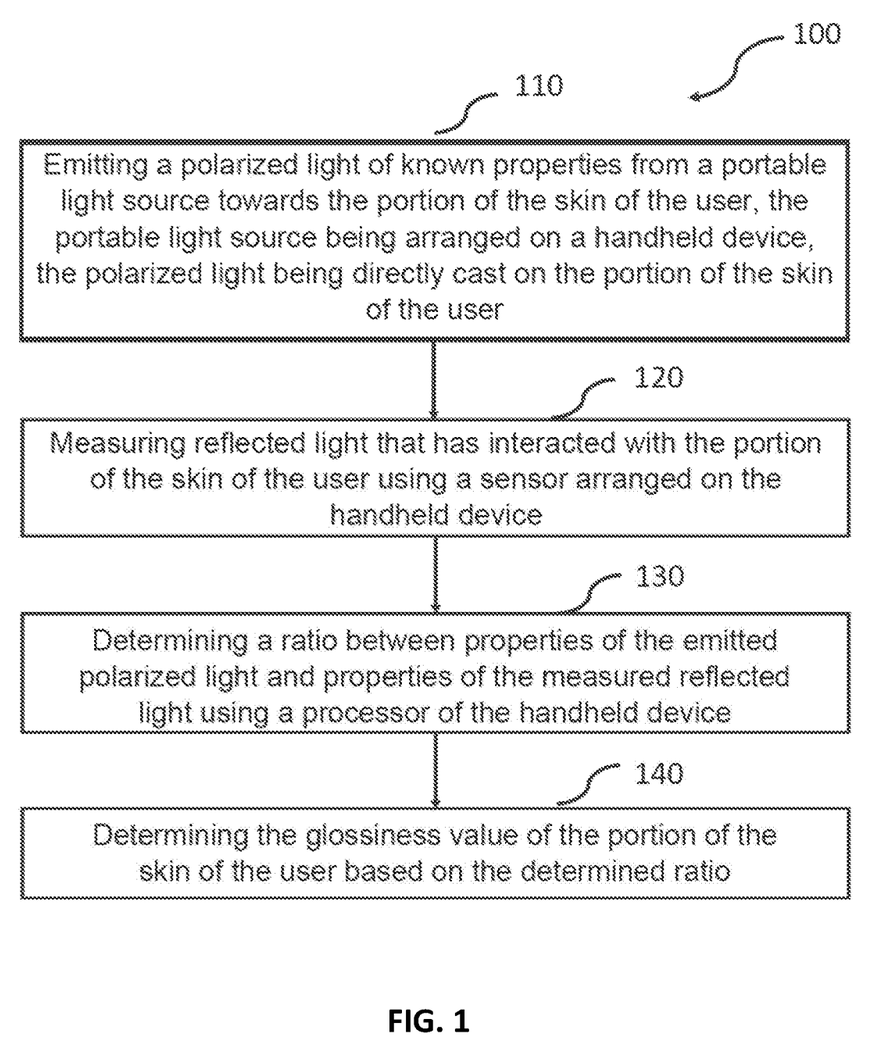
FIG. 1 is a flowchart summarizing steps of a method to determine a glossiness value of a portion of skin of a user in accordance with an exemplary embodiment.

In order to determine a glossiness value of the skin of a user, it is advantageous to follow the steps summarized in the flowchart of FIG. 1. FIG. 1 shows a method 100 for determining a glossiness value of the skin of a user in accordance with an exemplary embodiment. The value may be measured on different portions of the skin of a user, to differentiate between different body or face parts for more accurate estimations and product recommendations.

First, the method 100 includes emitting 110 a polarized light having known properties towards a portion of the skin of the user. This polarized light may have a known intensity, spectrum (generally, substantially monochromatic) and is emitted from a portable light source. The portable light source is arranged on a handheld device such as a smartphone, any other portable phone, a tablet, or a smart watch, for example. The portable light source can be an integral part of the handheld device or be a separate element such as a light emitting diode, arrangeable on the handheld device. To arrange such a separate portable light source on the handheld device, it is possible to use a magnetic fixture mechanism, a clip, an adhesive or a screw for example.

Then, the method proceeds by measuring 120 reflected light that has interacted with the portion of the skin of the user, using a sensor arranged on the handheld device.

This sensor can be a CCD camera, and can even be a camera that forms an integral part of the handheld device. Alternatively, the sensor can be arranged on the handheld device using similar fixture mechanisms to those described above in connection with the portable light source. In an embodiment, the sensor is arranged at an opposite edge of the handheld device, in order to be able to measure light reflected from an angle of about 60° on the portion of the skin of the user. A typical glossiness measurement would rely on incident light that is cast on the portion of the skin on the user with an incident angle comprised between about 5° and about 85°, preferably an angle comprised between about 40° and about 70°. Arranging the portable light source and the sensor at opposite edges of the handheld device takes advantage of the length of the handheld device. For example, when the handheld device is a portable phone, the length of the portable phone separates the light source from the sensor by a distance of about 15 cm, which creates conditions that allow an illumination of the portion of the skin with an incident angle of about 60° and detection of the reflected light, in close-up "selfie" configuration. In such a configuration, the user can hold the handheld device a few centimeters above the portion of the skin to measure the reflected light. The portable phone may also be used in another mode by arranging the light source and sensor at different edges of the handheld device, for example on a side of the handheld device opposite the one comprising a display.

Then, the light detected by the sensor is processed to compare its properties with those of the light emitted by the light source at a next step corresponding to a step of determining 130 the ratio of properties of the reflected light on the properties of the incident light, and therewith determining 140 the glossiness value. In particular, a ratio between the intensity of reflected light and the intensity of incident light can be calculated in order to establish a glossiness value. As is common practice in available glossmeters, this ratio can also be compared to a reference value, for example the same ratio obtained on a black glass with a known refractive index. Typically, this black glass can be a highly polished black glass with a refractive index of about 1,567 for the sodium D line, which is associated with a gloss value of 100. Ratios between incident light and reflected light on other surfaces is compared to this reference ratio and attributed a glossiness value number higher or lower than 100.

Other methods of defining the glossiness value can also be used.

Finally, in an embodiment, the method is completed by outputting or triggering the outputting of the determined glossiness value. This can be done by displaying the determined glossiness value on a display of the handheld device, or by transmitting this value to another device.

In the embodiment where the sensor is not an integral part of the handheld device, a transmission of the measured reflected light to a processor of the handheld device is possible. When the sensor is the camera of the handheld device for example, then the measured reflected light can be transferred to a processor of the handheld device to determine the glossiness value and display it to the user.

The handheld device may also output the glossiness value by vocally expressing it to the user (vocal output via a speaker of the handheld device or another appropriate device for example).

The method described above can be steered by the user using his handheld device and interacting with it via an app. In particular, such an app may guide the user throughout the process of emitting the polarized light, and measuring the reflected light, in particular by indicating how the handheld device should be positioned above the portion of the skin of the user.

In an embodiment, the app can receive inputs from the user, such as information about his age, skin color, and type of skin care products used, for example. The app may further use local information about weather and location to take into account other factors that might influence the glossiness value of the skin of the user.

In an embodiment, the glossiness value is output in the form of a number, for example, given in gloss units as described above. Alternatively, the glossiness value is a more qualitative assessment of the gloss of the portion of the skin of the user, for example, an information that the skin of the user has a low gloss value, a medium gloss value or a high gloss value.

In an embodiment, alongside an outputting of the gloss value, the method further outputs a product recommendation to the user. In particular, the method may access a database and pick a selection of non-therapeutic skin care products such as creams and lotions, to reduce the glossiness of skin.

These recommendations may be improved by querying via an app the effect that the user wants to achieve (reduce gloss, increase gloss, the time of day at which the effect is desired, for example).

The app can enable a monitoring of the evolution of the glossiness of the skin of the user by storing each value and time of measurement and comparing it to previous measurements. This may enable outputting more precise product recommendations or predict the future evolution of the glossiness of the skin of the user and adapt the product recommendation accordingly, further based on existing inputs from the user.

Figure 2:
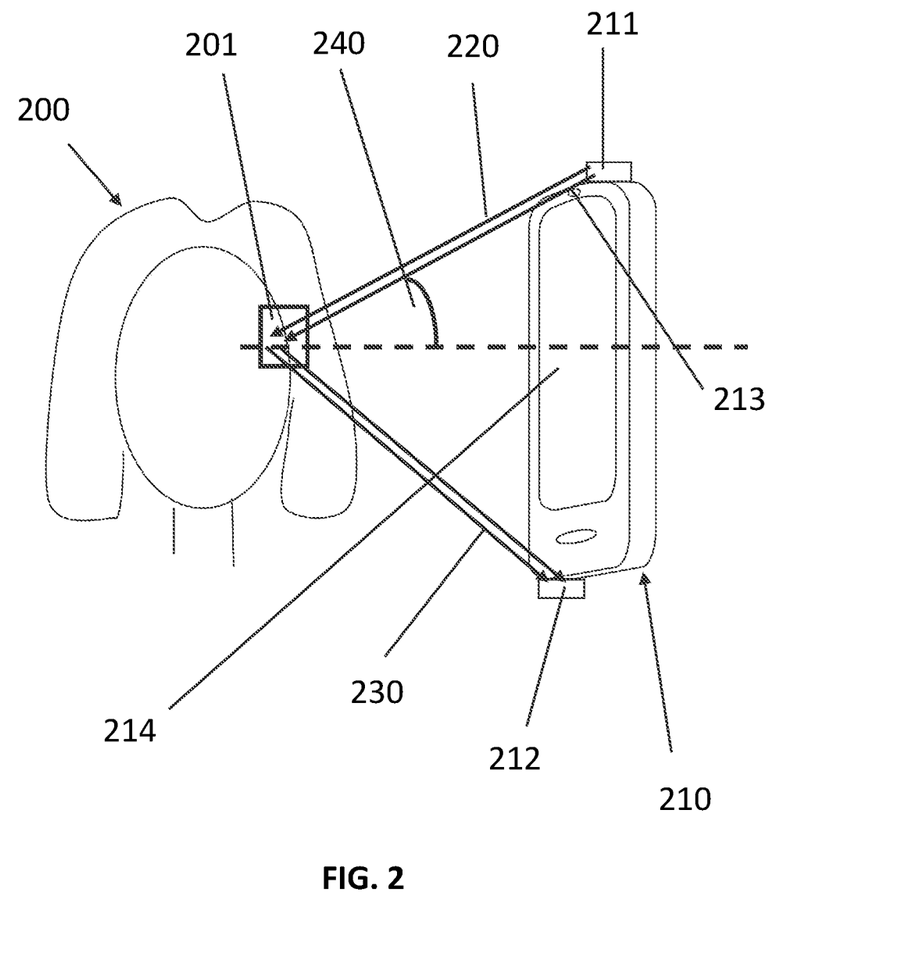
FIG. 2 is a schematic illustration of a handheld device, in accordance with an exemplary embodiment, equipped with a portable light source and a sensor, capable of implementing the method of FIG. 1.
Figure 3:
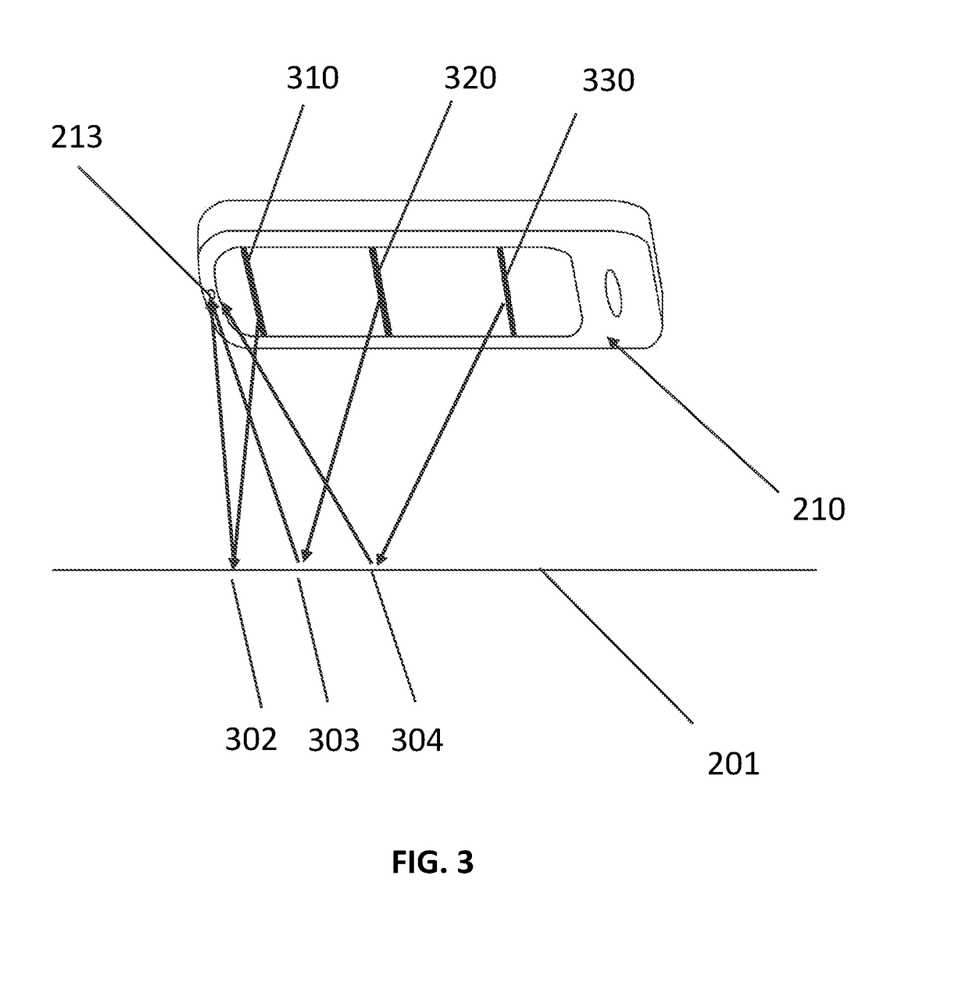
FIG. 3 is a schematic illustration of a handheld device used in a mode which projects light on the skin of a user with its display and measures reflected and scattered light with the camera of the handheld device in accordance with an exemplary embodiment.

FIG. 2 and FIG. 3 show two possible system arrangements for enabling implementation of the method contemplated herein.

In FIG. 2, in accordance with an embodiment, a user 200 with a portion 201 of skin is represented. A handheld device 210, in the form of a portable phone, is placed with its display 214 facing the portion 201 of the skin of the user 200. A portable light source 211 is fixed onto one edge of the handheld device 210 and emits polarized light 220 towards the portion 201 of the skin of the user 200. In an embodiment, the angle of incidence 240 of this light is at 60°, but other angles are acceptable, provided a sensor 212 at another edge of the handheld device allows measurement of the reflected light on the portion 201 of the skin of the user 200.

Reflected light 230 arrives at the sensor 212.

In an embodiment, the handheld device 210 comprises a camera 213 which also serves as the sensor 212. In that case, the portable light source could for example be arranged at the lower edge of the handheld device 210 as represented on FIG. 2. The display 214 of the handheld device 210 can also serve as the portable light source, or as an additional light source emitting the same light as the portable light source 211. This second light can be used to measure, at different angles of incidence, light scattered by the skin of the user, in order to subtract the contribution of skin color or particular skin features to the glossiness value that is determined. This feature consisting in recording light scattered by skin in order to measure its gloss value more accurately is already known from existing glossmeters. Glossmeters of the prior art typically measure the scattered light at an angle of incidence of 0°. The systems and methods contemplated herein may measure scattered light at different angles, depending on the relative position of the light source (separate element such as portable light source 211, or the display 214 of the handheld device 210).

FIG. 3 shows a different embodiment, that can also be implemented together with the one of FIG. 2. In FIG. 3, the portable light source is inside the display of the handheld device 210. The polarized light is emitted by activating a part 310, 320, 330 of the display. This region is advantageously a stripe or spot, but can be the whole screen of the handheld device as well or any other pattern therein. The app that can be used to determine the glossiness value of the portion of the skin of the user can activate parts 310, 320, 330 in a sequence, for example as a scanner. This will illuminate the portion of the skin of the user with different incident angles and the point of reflection 302, 303, 304 on the skin will vary accordingly. This method can be used to determine an average glossiness value over a portion of the skin of a user extending over a few cm, thereby also avoiding inaccurate determinations due to the presence of irregularities on the skin of the user.

In an embodiment, the steps of the examples and embodiments described above can be implemented by a processor such as a computer. A computer program product comprising steps of the above-described method can be used to implement the method on a computer.

Different types of non-transitory computer readable storage mediums on which a computer program comprising instructions to implement the methods contemplated herein can be used. These could for example comprise a processor or chip, an electronic circuit comprising several processors or chips, a hard drive, a flash or SD card, a USB stick, a CD-ROM or DVD-ROM or Blue-Ray disc, or a diskette or floppy disk.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for determining a glossiness value of a portion of a skin of a user, the method comprising the steps of:
   emitting a polarized light having a property value from a portable light source towards the portion of the skin of the user, the portable light source coupled to a handheld device, the polarized light being cast on the portion of the skin of the user from the portable light source;
   measuring reflected light reflected from the portion of the skin of the user using a sensor coupled to the handheld device, the reflected light having a property value;
   determining a ratio between the property value of the emitted polarized light and the property value of the measured reflected light using a processor of the handheld device;
   determining the glossiness value of the portion of the skin of the user based on the determined ratio, and
   outputting or triggering an outputting of the determined glossiness value.

2. The method of claim 1, wherein the portable light source is integral with the handheld device.

3. The method according to claim 2, wherein the portable light source comprises part of a display of the handheld device, the method further comprising:
   activating a part of the display of the handheld device to emit the polarized light.

4. The method according to claim 3, further comprising:
   activating different parts of the display of the handheld device, the different parts differing by a distance separating the different parts of the display of the handheld device from the sensor.

5. The method according to claim 4, wherein the different parts of the display of the handheld device are activated sequentially.

6. The method according to claim 1, wherein the polarized light of known properties is cast on the portion of the skin of the user with an incident angle comprised between about 10° and about 75°.

7. The method according to claim 1, further comprising:
   measuring light scattered by the portion of the skin of the user.

8. The method according to claim 7, wherein the scattered light is measured with a camera of the handheld device.

9. The method according to claim 1, wherein the handheld device is chosen from the group comprising: a portable phone, a tablet, and a smart watch.

10. The method according to claim 1, wherein determining the glossiness value of the portion of the skin of the user based on the determined ratio, and outputting or triggering an outputting of the determined glossiness value comprise:
    recording a glossiness value determined for the portion of the skin of the user at a first time;
    recording a glossiness value determined for the portion of the skin of the user at a second time differing from the first time; and
    outputting an evolution of a glossiness of the portion of the skin of the user based on the glossiness value determined at the first time and the glossiness value determined at the second time.

11. The method according to claim 1, further comprising:
    determining a recommended non-therapeutic skin care product for the portion of the skin of the user based on the determined glossiness value; and
    outputting a reference identifying the determined recommended non-therapeutic skin care product.

12. A system for determining a glossiness value of a portion of a skin of a user, the system comprising:
    a portable light source configured to emit polarized light having a property value towards the portion of the skin of the user so that the polarized light is cast on the portion of the skin of the user from the portable light source;
    a sensor configured to measure reflected light reflected from the portion of the skin of the user, the reflected light having a property value;
    a handheld device comprising a processor configured to:
       determine a ratio between the property value of the emitted polarized light and the property value of the measured reflected light; and
       determine the glossiness value of the portion of the skin of the user based on the determined ratio;
    wherein the portable light source and the sensor are physically coupled to the handheld device.

13. The system according to claim 12, wherein the portable light source is physically integral with the handheld device.

14. The system according to claim 12, wherein the sensor is physically integral with the handheld device.

15. The system according to claim 12, wherein the portable light source is removably connected to the handheld device.

16. The system according to claim 12, wherein the sensor is removably connected to the handheld device.

17. The system according to claim 12, wherein the processor is further configured to output or trigger an output of the determined glossiness value.

18. The system according to claim 12, wherein the portable light source comprises part of a display of the handheld device and wherein the handheld device is configured to activate the part of the display to emit the polarized light.

19. The system according to claim 18, wherein the part of the display comprises different parts of the display of the handheld device, the different parts differing by a distance separating the different parts of the display of the handheld device from the sensor.

20. A non-transitory computer readable storage medium embodying a computer program product, the program product comprising a program for determining a glossiness value of a portion of a skin of a user, the program configured to:
- emit a polarized light having a property value from a portable light source towards the portion of the skin of the user, the portable light source coupled to a handheld device, the polarized light being cast on the portion of the skin of the user from the portable light source;
- measure reflected light reflected from the portion of the skin of the user using a sensor coupled to the handheld device, the reflected light having a property value;
- determine a ratio between the property value of the emitted polarized light and the property value of the measured reflected light using a processor of the handheld device;
- determine the glossiness value of the portion of the skin of the user based on the determined ratio, and
- output or trigger an output of the determined glossiness value.

\* \* \* \* \*